(12) United States Patent
Verschuur (10) Patent No.: US 6,375,610 B2
(45) Date of Patent: *Apr. 23, 2002

(54) ENDOSCOPIC DRAPE (75) Inventor: Mark Verschuur, Lilydale (AU)

(73) Assignee: Fairmont Medical Products Pty. Ltd. (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/356,220

(22) Filed: Jul. 16, 1999

Related U.S. Application Data (63) Continuation-in-part of application No. PCT/AU98/00036, filed on Jan. 23, 1998.

(30) Foreign Application Priority Data

Jan. 23, 1997 (AU) .............................. PO-4783

(51) Int. Cl.[7] .................................................. A61B 1/00
(52) U.S. Cl. ...................... 600/122; 600/112; 600/125; 359/510; 359/507
(58) Field of Search ................................ 600/122, 125, 600/112, 136; 359/507, 510; 206/438, 316.1; 128/898

(56) References Cited

U.S. PATENT DOCUMENTS

| 4,522,196 A | * | 6/1985 | Cunningham et al. | 128/4 |
| 5,274,500 A | * | 12/1993 | Dunn | 359/507 |
| 5,301,647 A | | 4/1994 | Lafferty et al. | |
| 5,311,358 A | * | 5/1994 | Penderson et al. | 359/510 |
| 5,325,846 A | * | 7/1994 | Szabo | 128/4 |
| 5,433,221 A | * | 7/1995 | Adair | 128/849 |
| 5,467,223 A | * | 11/1995 | Cleveland, Jr. et al. | 359/510 |
| 5,498,230 A | | 3/1996 | Adair | |
| 5,591,119 A | * | 1/1997 | Adair | 600/112 |
| 5,682,264 A | * | 10/1997 | Cleveland et al. | 359/510 |
| 5,792,045 A | * | 8/1998 | Adair | 600/125 |
| 5,876,328 A | * | 3/1999 | Fox et al. | 600/122 |
| 5,882,295 A | * | 3/1999 | Kope | 600/122 |

FOREIGN PATENT DOCUMENTS

| WO | WO96/17558 | | 6/1996 |
| WO | WO 96/27322 | * | 9/1996 |
| WO | WO96/27322 | | 9/1996 |
| WO | WO97/32534 | | 9/1997 |

* cited by examiner

Primary Examiner—John P. Leubecker
Assistant Examiner—Jocelyn Ram
(74) Attorney, Agent, or Firm—Wallenstein & Wagner, Ltd.

(57) ABSTRACT

A method for producing an endoscopic drape includes positioning a portion of a sheath of flexible material (22) in abutment with a joining portion (23) of a first housing piece (14). A joining portion (24) of a second housing piece (16) is positioned close to joining portion (23) and the joining portions are then joined together, for example, by ultrasonic welding. This forms a housing (12) in which the portion of the sheath (22) is entrapped between the first housing piece (14) and the second housing piece (16). The portion of the sheath (22) may be joined to the first housing piece (14) by a thermoplastic gasket or o-ring (35) prior to joining the first and second housing pieces (14, 16) to improve the seal between the sheath (22) and the housing (12). The housing (12) includes a clear lens or window (27) that provides an optical pathway through the housing and also provides a sterility barrier.

32 Claims, 5 Drawing Sheets

ENDOSCOPIC DRAPE

This Application is a Continuation-In-Part of International Application No. PCT/AU98/00036, filed Jan. 23,1998 (claiming priority from Australian Provisional Appln. No. PO 4783, filed Jan. 24, 1997), now pending (which is hereby incorporated by reference).

Priority of foreign Application No. PCT/AU98/00036 filed Jan. 23, 1998 in Australia is claimed under 35 U.S.C. 119(a)–(d).

The present invention relates to a method for manufacturing a drape for use in endoscopic surgery and to a drape for use in endoscopic surgery.

Endoscopic surgery is a low-invasive surgical technique. Also known as keyhole surgery, endoscopic surgical procedures require that only small incisions be made in the skin, which minimises damages to muscle, skin and tissue. In endoscopic surgical procedures, thin, elongate medical instruments are passed through one or more incisions in the skin. In order to provide the surgeon with a view of the site of the operation (the actual site of the operation is covered by the skin), it is usual to use an endoscopic telescope to supply pictures to a camera and from there to a visual display unit, such as a television screen. The endoscopic telescope is easily sterilised by autoclaving and this is necessary because the telescope has one end thereof inserted through an incision in the patient during the operation. The other end of the telescope is optically linked to the camera and the camera sends pictures of the operating site to the visual display unit. Unfortunately, the camera is normally not able to be sterilised by autoclaving because autoclaving would damage the optical components of the camera.

The camera is optically linked to the telescope and this may represent a potential breach of the sterile field. To avoid potential difficulties with breach of the sterile field, it has become common practice to cover the unsterile camera and its associated cable with a sterile cover.

One such sterile cover is disclosed in U.S. Pat. No. 4,914,521 in the name of Adair. This patent discloses an apparatus for enclosing a non-sterile camera and its trailing cable. The apparatus includes a sterile cylindrical housing for receiving a camera at one end and a flared annular mounting for receiving an optical transmitting means, such as an endoscopic and associated "C" mount at its other end. The housing includes a clear window that is located between the endoscope and the lens of the camera and that allows light to pass from the endoscope to the camera. The clear lens also acts as a bacteria barrier between the camera and the endoscope. A plastic sleeve is attached to the outer part of the housing by adhesive tape. In use, the sleeve (which is sterile) is pulled back over the camera cable to maintain sterility about the camera cable.

International Patent Application No. PCT/US95/14735 (publication No. WO 96/17558) also in the name of Adair discloses a surgical drape that allows greater flexibility in use than that described in U.S. Pat. No. 4,914,521. Again, the drape includes a housing having a sterile sleeve positioned over a neck portion of the housing such that a fluid and air tight seal is formed. Typically, the seal between the sleeve and the housing is formed by surgical tape, adhesives, shrink wrapping or use of double-faced adhesive strips.

A potential difficulty with the apparatus described in U.S. Pat. No. 4,914,521 and WO 96/17558 resides in the use of adhesives or similar means to join the sleeve to the housing. In practice, it can prove to be difficult to obtain a leak-proof seal that will be effective in maintaining sterility.

The present invention provides a method and an apparatus that overcomes or at least ameliorates the above-mentioned disadvantage of the prior art.

In a first aspect, the present invention provides a method for manufacturing a drape for use in endoscopic surgical procedures, the method including the steps of positioning a portion of a sheath of flexible material adjacent to or in abutment with a joining portion of a first housing piece, positioning a joining portion of a second housing piece adjacent to or in abutment with the portion of the sheath and the joining portion of the first housing piece and joining the joining portions of the first housing piece and the second housing piece to thereby form a housing and entrap the portion of the sheath between the first housing piece and the second housing piece.

The portion of the sheath is preferably an end of the sheath. Preferably, an edge of the portion of the sheath is entrapped between the first housing piece and the second housing piece.

Preferably the sheath of flexible material is generally cylindrical in shape. The distal end of the sheath is fitted between the two housing pieces with an edge of the distal end overlapping part of the joining portions of the two housing pieces. Subsequent joining of the two housing pieces to form the housing also entraps, or crimps, the end of the sheath between the two housing pieces and this ensures that a leak-proof seal is formed between the housing and the sheath. It is not necessary to use tape or adhesive to join the end of the sheath to the outer wall of the housing. Rather, the end of the sheath is trapped or crimped within the housing.

The housing pieces may suitably be made from plastics material. A suitable material may be general purpose polystyrene mixed with a blend of K-resin. This material is gamma-ray stable and can be transparent. Another suitable material may be an ABS mixture or blend, which lends itself to ultrasonic welding.

The housing may include a camera coupling for coupling a camera thereto. The sheath is then pulled along the cable extending from the cable to cover the non-sterile cable with the sterile sheath.

The housing may also include a telescope coupling for coupling an endoscopic telescope thereto. Throughout this specification, the term "telescope" is considered to include any device used in endoscopic surgery to transmit an optical signal to the camera.

Most preferably, the housing includes a camera coupling and a telescope coupling. In this embodiment, the drape provides a convenient means for optically linking the telescope to the camera whilst maintaining sterility in the sterile field. It is preferred that one of the first or second housing pieces includes the camera coupling and that the other of the first or second housing pieces includes the telescope coupling. In this arrangement, the housing can be assembled by joining two pieces. However, it will be appreciated that the camera coupling and/or the telescope coupling could comprise separate pieces that can be connected or joined to the first and/or second housing pieces. In such cases, the complete housing comprises the first and second housing pieces joined together and the camera coupling and/or telescope coupling connected thereto.

The housing preferably includes an optically clear pathway between the telescope coupling and the camera coupling to allow good quality pictures of the operating site to be transmitted to the visual display unit. The optically clear pathway may be provided by producing the housing from transparent material. Alternatively, a clear window or lens may be included within the housing.

If a clear window or lens is used, the window or lens is preferably located between the position of the camera (in use) and the telescope so that the window acts as a barrier. Indeed, it will be appreciated that the housing should include a barrier between the camera and the telescope to maintain sterility and to exclude the non-sterile camera from the sterile field.

The joining portion of the first housing piece preferably comprises a joining face. Similarly, the joining portion of the second housing piece preferably comprises a joining face. To join the housing pieces together, the joining faces are placed closely adjacent to or in abutment with each other (with the edge of the end of the sheath therebetween) and the joining faces are joined together at at least a portion of their faces.

In embodiments where the first and second housing pieces are made from plastics material, the first and second housing pieces are preferably joined by ultrasonic welding. The joining portion of one of the first or second housing pieces may include an energy director to enhance the ultrasonic weld. The energy director may comprise a raised ridge extending around the joining portion and preferably being located towards the centre of the joining portion.

As mentioned above, the end of the sheath is trapped between the first and second housing pieces when they are joined together to form a leak-proof seal. The seal between the sheath and the housing may be improved by positioning a thermoplastic material between the end of the sheath and one of the joining portions. The thermoplastic material is a material that can melt and adhere to the material of the sheath. Once the end of the sheath has been placed over the joining portion, the sheath material may be impulse sealed to the joining portion via the thermoplastic material. The thermoplastic material is preferably a thermoplastic rubber (TPR). The thermoplastic material may be in the shape of a gasket or an "O"-ring. To assist in positioning the gasket or O-ring, a groove may be formed on the associated joining portion and the gasket or O-ring placed in the groove. It is believed that use of a thermoplastic material, such as a TPR gasket or O-ring, will assist in improving the seal formed between the sheath and the housing. Indeed, it is believed that use of the thermoplastic material should result in the formation of a water-tight, leak proof seal which will thus form a sterility barrier. However, it will be appreciated that a leak proof seal between the sheath and the housing may be obtained without use of the thermoplastic material.

In another embodiment, the method of the present invention includes the steps of providing a thermoplastic material on the first housing piece, positioning the portion of the sheath over the thermoplastic material and adjacent to or in abutment with the joining portion of the first housing piece, joining the sheath to the thermoplastic material, and subsequently joining the first and second housing pieces.

In a preferred form of this embodiment, the invention further includes the steps of placing a lens in the first housing piece prior to joining the first and second housing pieces. Alternatively, the lens may be placed in the second housing piece prior to joining the first and second housing pieces. The lens may be placed in the first housing piece either before or after the thermoplastic material and sheath are joined. The step of joining the first and second housing pieces may act to affix the lens in the housing, for example, by ultrasonic welding. Alternatively, the lens may be affixed to either of the first housing piece or second housing piece prior to joining the first and second housing pieces.

The thermoplastic material may be joined to the sheath by welding, such as impulse welding. The thermoplastic material preferably comprises a gasket. The gasket may be placed in a groove formed in the first housing piece.

In some instances, the sheath may extend across the optical pathway in the housing. If the sheath is made from a material that will affect optical clarity or quality, the sheath material is preferably removed from the optical pathway prior to joining the first and second housing pieces together or after joining the first and second housing pieces together.

The camera coupling and telescope coupling of a preferred embodiment of the present invention may be any suitable couplings known to the skilled person. The camera coupling is preferably a "C" coupling that is widely used in endoscopic procedures and need not be discussed farther.

The sheath is preferably made from thin film plastics material. Polyethylene is a suitable material for the sheath. The sheath is preferably transparent. The sheath may be rolled up or folded in a telescopic or accordion-like manner to facilitate positioning of the sheath over the camera cable. The proximal end of the sheath may be fitted with a pull-tab to simplify positioning of the sheath. One or more resealable adhesive tabs may be placed on the sheath to enable the sheath to be closely conformed to the cable.

In some embodiments of the present invention the material of the sheath may not readily join to the material of the housing pieces. In such cases, it is preferred that the sheath is positioned between the housing pieces such that the sheath does not fully cover or extend fully between the joining portions of the housing pieces. This allows at least a part of one joining portion to be in contact with at least a part of the other joining portion. The joining procedure then joins the parts of the joining portions in contact with each other.

To improve the seal between the end of the sheath and the housing, the joining portions of the first and second housing pieces may have a degree of surface roughness, surface serrations, or the like, to improve mechanical contact between the sheath and the housing. When the housing pieces are joined to form the housing, the first and second housing pieces are located very close to each other and thus sandwich the end of the sheath between them. The surface roughness, surface serrations or the like assist in holding the sheath in the housing. Moreover, if ultrasonic welding is used to join the two housing pieces, molten plastic from the housing pieces may flow around the edge of the end of the sheath to further hold the sheath.

The present invention also encompasses a drape. In accordance with a second aspect, the present invention provides a drape for use in an endoscopic surgical procedure, the drape including a housing comprising a first housing piece joined to a second housing piece and a sheath of flexible material having a portion thereof connected to the housing, wherein the sheath is connected to the housing by positioning a portion of the sheath between the first housing piece and the second housing piece prior to joining the first and second housing pieces and wherein the portion of the sheath is trapped between the joined first and second housing pieces to thereby establish a leak-proof seal between the sheath and the housing.

Preferably, the portion of the sheath is an end of the sheath. Preferably, the portion of the sheath is joined to one of the first or second housing pieces by joining the sheath to a thermoplastic material positioned on the one of the first or second housing pieces prior to joining the first and second housing pieces.

The housing preferably further comprises a camera coupling for coupling a camera thereto and a telescope coupling for coupling a telescope thereto, the housing effective to establish an optical link between the telescope and the camera. The housing should provide an optically clear pathway between the telescope and the lens of the camera.

The housing should also include a barrier between the camera and the telescope to preserve sterility in the sterile field. The combination of the sterile barrier within the housing and the sterile sheath that may be draped over the camera and its associated cord ensures that the non-sterile camera does not compromise the sterile field.

The telescope coupling may comprise a "C"-coupling that is well known to skilled persons. Any other suitable coupling may also be used as the telescope coupling. Similarly, the camera coupling may comprise any suitable coupling known to the skilled person. The telescope coupling and/or camera coupling may be formed integrally with the first and second housing pieces, or they may comprise additional pieces to be connected to the housing.

In a third aspect, the present invention provides a drape for use in an endoscopic surgical procedure, the drape including a housing including a first housing piece having a joining portion joined to a joining portion of a second housing piece, a sheath of flexible material having a portion positioned between the first and second housing pieces, a thermoplastic material positioned between the portion of the sheath and one of the first and second housing pieces, the thermoplastic material affixing the portion of the sheath to the one of the first and second housing pieces and wherein the joining portions of the first and second housing pieces surround and entrap an edge of the portion of the sheath in the completed housing.

The housing of the drape of the second and third aspects of the invention preferably includes a lens positioned between the first and second housing pieces.

In another aspect the present invention provides a drape for use in an endoscopic surgical procedure comprising a housing and a sheath of flexible material joined to the housing to form an essentially leak-proof seal between the sheath and the housing, the housing having a camera coupling means for coupling a camera thereto and a telescope coupling means for coupling an endoscopic telescope thereto, the housing having an optical pathway therein to enable light and/or an image from the endoscopic telescope to be transmitted to the camera, wherein a corrective lens is placed in the optical pathway.

The housing of the drape acts as an adaptor for connecting the camera and the telescope. Instead of the camera and telescope being directly connected to each other, the housing is positioned between the camera and the telescope with the camera and the telescope each connected to the housing. This acts to interpose a member between the camera and the telescope which results in the respective ends of the camera and telescope being separated somewhat during the oration. This may result in the image from the telescope not being properly focussed on the camera, which can result in the image from the camera that is displayed on the visual display unit during the operation being out of focus. The corrective lens incorporated into the housing overcomes this problem. As a further advantage, the corrective lens also acts to enhance or maintain the size of the picture on the visual display unit.

The corrective lens preferably has a corrective power sufficient to produce an in-focus picture on the visual display unit during the operative procedure. A lens with a power of from 1 to 10 dioptive is preferred, more preferably about 2.0 dioptive.

The drape of the present invention is preferably made in accordance with the first aspect of the present invention, as described hereinabove. In this method, the housing is made from first and second housing pieces joined together, with the sheath entrapped between the first and second housing pieces.

The lens preferably is an anti-fog lens or has an anti-fog coating applied thereto in order to minimise fogging during use. For example, the lens may be made from an anti-fog material or it may be sprayed or coated with an anti-fog material.

The telescope coupling means may be any conventional coupling means known by the person of skill in the art to be suitable. A conventional "C" coupling is one example. Similarly, the camera coupling means may be any convention coupling means known to be suitable to a person of skill in the art.

The sheath is preferably made from thin film plastics material. Polyethylene is a suitable material for the sheath. The sheath is preferably transparent. The sheath may be rolled up or folded in a telescopic or accordion-like manner to facilitate positioning of the sheath over the camera cable. The proximal end of the sheath may be fitted with a pull-tab to simplify positioning of the sheath. One or more resealable adhesive tabs may be placed on the sheath to enable the sheath to be closely conformed to the cable.

In yet another aspect, the present invention provides la drape having a housing in which the telescope coupling means can allow at least a degree of rotation of the telescope or substantially prevent rotation of the telescope.

In this aspect the present invention provides a drape for use in an endoscopic surgical procedure comprising a housing and a sheath of flexible material joined to the housing to form an essentially leak-proof seal between the sheath and the housing, the housing having a camera coupling means for coupling a camera thereto and a telescope coupling means for coupling an endoscopic telescope thereto, the housing having an optical pathway therein to allow light and/or an image from the telescope to be transmitted to the camera, wherein the telescope coupling means includes locking means operative between a first position wherein the telescope is connected to the telescope coupling means and can rotate within the telescope coupling means and a second position where the telescope is connected to the telescope coupling means and locked against rotation within the telescope coupling means.

The drape of the present invention preferably includes the corrective lens of the one aspect of the invention and the locking means of another aspect of the invention.

Preferred embodiments of the present invention will now be described with reference to the drawings. It is to be understood that the drawings are intended to illustrate the present invention and should not be considered to limit the invention.

Figure 1:
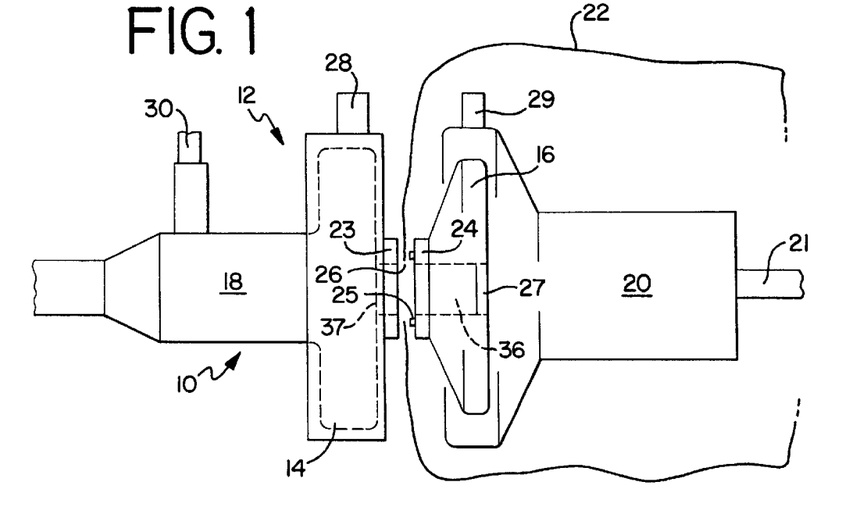
FIG. 1 shows a side view of the apparatus in accordance with the present invention.

The apparatus 10 in accordance with the present invention shown in FIG. 1 includes a housing 12 comprising a first housing piece 14 and a second housing piece 16. The first housing piece 14 provides a coupling for endoscopic telescope 18 to be coupled thereto. The second housing piece 16 provides a coupling for coupling camera 20 thereto. The apparatus further includes a sheath of flexible material 22 that, in use, is adapted to be placed over and surround camera 20 and the associated camera cable 21. Sheath 22 thereby enables the unsterile camera 20 and camera lead 21 to be contained within a sterile sheath.

Housing 14 includes a joining portion 23 that is able to be abutted onto a complementary joining portion 24 on housing piece 16. Joining portion 24 of housing piece 16 includes an energy director 25 in the form of a circular raised ridge.

The distal end of sheath 22 is provided with a hole that is defined by edge 26. In order to form the apparatus 10 shown in FIG. 1, the distal end of sheath 22 is positioned such that the end 26 lies over joining portion 25 of housing piece 16. Housing piece 14 is then positioned such that housing portion 23 either abuts or is closely adjacent to the edge 26 of sheath 22 and joining portion 24 of housing piece 16. The joining portions 23, 24 are then joined together by ultrasonic welding to thereby form housing 12. This step also acts to entrap the end of sheath 22 between the now connected housing pieces and this ensures that the end of sheath 22 is connected to the housing in a manner that ensures a leak proof seal is obtained.

Housing piece 16 further includes a clear lens 27 that aligns with the lens of the camera when the camera is connected to the housing. This ensures that an optically clear pathway is obtained from the telescope to the camera lens. Moreover, it also ensures that a bacteria barrier exists between the housing piece 16 and the camera 20.

The piece 12 further includes a conventional "C" coupling 28 that is used to couple the telescope to the housing. The camera includes a conventional coupling 29 that enables the camera to be coupled to the housing piece 16. Both "C" coupling 28 and camera coupling 29 are conventional items used in endoscopic apparatus and need not be discussed further.

It is also noted that the telescope 18 includes a fibre-optic port 30 to enable connection of a fibre-optic light source to the telescope.

Figure 2:
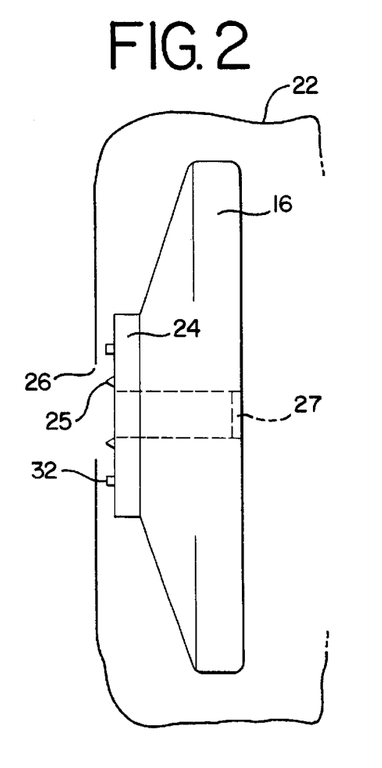
FIG. 2 shows an expanded view of the housing piece that comprises a camera coupling with the sheath positioned ready for manufacture.

FIG. 2 shows an expanded vies of second housing piece 16 and sheath 22. As can be seen from FIG. 2, the edge 26 defining the hole in the end of the sheath 22 is positioned such that the end of the sheath 22 does not cover all of joining portion 24 of housing piece 16. This ensures that the joining portion 23 of housing piece 14 can come into contact with and be joined to at least the inner portion of housing portion 24, which assists in ensuring that a good join between housing piece 16 and housing piece 14 is achieved even if the material of sheath 22 is not compatible with ultrasonic welding to the housing pieces 16, 14.

FIG. 2 also shows a thermo-plastic rubber gasket or O-ring 32 that is positioned in a groove or channel formed in the surface of joining portion 24. The gasket or O-ring 32 is positioned such that it comes into contact with the end of the sheath 22. The gasket or O-ring 32 is made from a material that is compatible for joining with the material of sheath 22 and thus the gasket or O-ring 32 can further assist in obtaining a leak proof seal. Thermoplastic rubber (TPR) is a suitable material for the gasket or O-ring.

Figure 3:
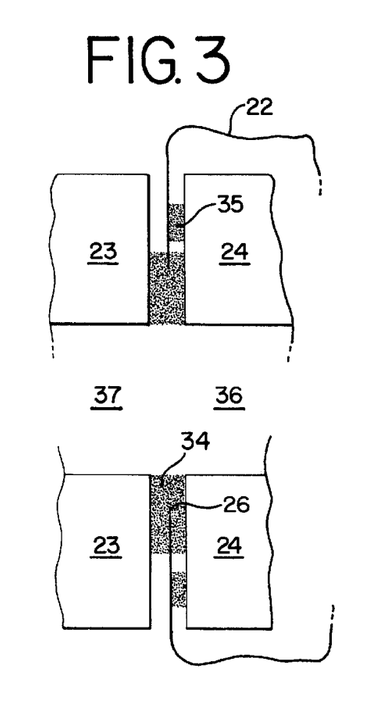
FIG. 3 shows an expanded view of the joining portions of the housing pieces and the sheath after the housing has been completed by joining the joining portions.

FIG. 3 shows an expanded view of the joining faces 23, 24 after they have been joined. As can be shown in FIG. 3, ultrasonic welding causes melting of joining portions 23, 24 in places where they abut and the molten plastic, shown by reference numeral 34 connects joining portions 23, 24 together. Preferably, the molten plastic 34 also extends around the edges 26 of sheath 22.

To further improve the quality of the join, the TPR gasket 32 is also impulse joined to the sheath 22. This results in a mass of molten plastic 35 being formed which can adhere to the material of the sheath 22.

In FIGS. 1 and 3, the spacing between joining portions 23 and 24 has been exaggerated to clearly show the construction of the apparatus. However, it will be appreciated that in the completed article joining portions 23 and 24 will essentially be in abutment or closely adjacent and they will be so closely spaced that the sheath 22 will be trapped therebetween.

The apparatus shown in FIGS. 1, 2 and 3 includes a passageway 36 formed in housing portion 22 and a passageway 37 formed in housing portion 14. These passageways are in alignment in the completed article and provide an optically clear pathway between the telescope and the camera. It will be appreciated that if the housing 12 is manufactured from a transparent plastic material, passageways 36, 37 need not be provided as the material of the housing itself can provide an optically clear pathway.

In FIGS. 1, 2 and 3, the sheath is shown in its extended position. However, it will be appreciated that the sheath will normally be provided in a rolled up or accordion folded manner to enable compact packaging to be achieved.

Once the housing has been manufactured, the apparatus 10 is packaged in sterile packaging. In order to use the apparatus, the scrub nurse opens the sterile packaging and connects the endoscope 18 to the housing. The unsterile camera 20 is inserted into the sheath 22 and connected to the housing. The sheath 22 is then unrolled or unfolded out along the camera and its trailing cable 21 so that the camera and the training cable are surrounded by the sterile sheath 22. To assist in positioning the sheath over the camera and cable, the end of the sheath may be provided with a pull tab. In order to enable to sheath to be closely conformed to the shape of the camera and the trailing cable, one or more resealable adhesive tabs may be provided on the sheath.

If it is desired to change the telescope during use, the telescope can be easily uncoupled and a new telescope engaged without compromising the sterile field.

After use, the telescope is uncoupled and the camera encased in the sheath is removed from the sterile field. The camera is then uncoupled and removed from the sheath and the apparatus 10 discarded for disposal.

Figure 4:
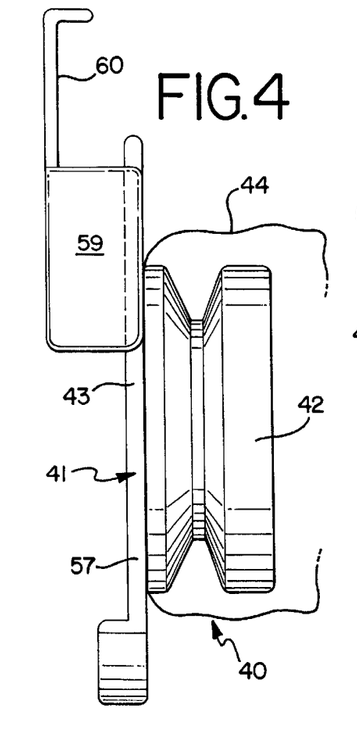
FIG. 4 shows an end view of a drape in accordance with another embodiment of the present invention.

FIGS. 4 to 13 relate to another embodiment of the present invention. As shown in FIG. 4, the drape 40 includes a housing 41 having a first housing piece 42 and a second housing piece 43. Housing pieces 42 and 43 are joined together to form housing 41. A sheath 44, which is of a generally cylindrical shape and made from a flexible plastic material is connected to housing 41.

Figure 5:
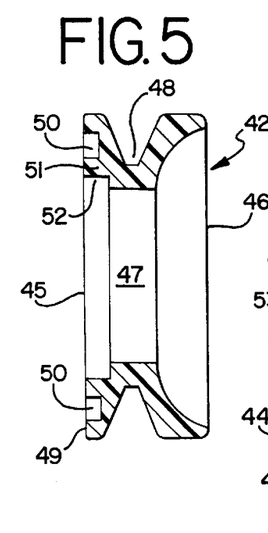
FIG. 5 shows a cross-sectional side view of the first housing piece of the drape of FIG. 4.

FIG. 5 shows a cross-sectional view of first piece 42. First piece 42 has a joining end 45 and a distal end 46. A passage 47 is formed in a first piece 42 and passage 47 provides an optical pathway between an endoscopic telescope and an endoscopic camera. First piece 42 includes a cylindrical region of reduced diameter 48, which provides a means for coupling an endoscopic camera (not shown) to the first piece 42.

Joining end 45 of first piece 42 has an outer annular surface 49 that surrounds a groove 50. Groove 50 extends substantially around the joining face 45 of first piece 42. The inner end of groove 50 is defined by an inner annular portion 51. A recessed, inner most annular portion 52 extends around the central passage 47. As can be seen from FIG. 5, the inner most annular portion 52 defines a shoulder.

Figure 6:
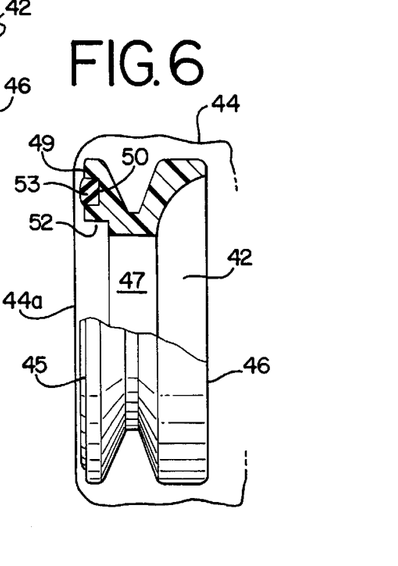
FIG. 6 shows the first housing piece of FIG. 5 with the sheath positioned and ready for joining to the first housing piece.

As shown in FIG. 6, a gasket or O-ring 53 is positioned in groove 50. Gasket or O-ring 53 is made from a thermoplastic material, such as TPR.

In order to manufacture the drape shown in FIG. 4, sheath 44 is positioned over the joining face 45 of first housing piece 42 such that a portion 44a of sheath 44 extends over the joining face. As can be seen from FIG. 6, portion 44a comes into contact with gasket or O-ring 53.

Figure 7:
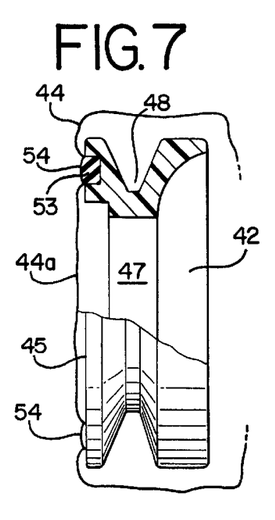
FIG. 7 shows the arrangement of FIG. 6 with the sheath joined to the first housing piece.
Figure 8:
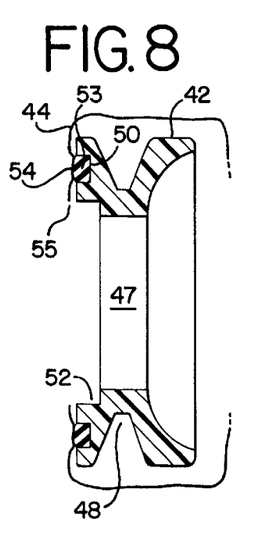
FIG. 8 shows the arrangement of FIG. 7 with excess sheath material removed for optical clarity.

Once the portion 44a of sheath 44 has been properly positioned, impulse welding is used to join the portion 44a to the gasket or O-ring 53. This is best shown in FIG. 7 where portion 54 of the sheath 44 has been joined to the gasket or O-ring 53. It will be appreciated that the process of impulse welding causes the gasket or O-ring 53 to at least partially melt and to thereby join to portion 54 of the sheath 44.

Figure 9:
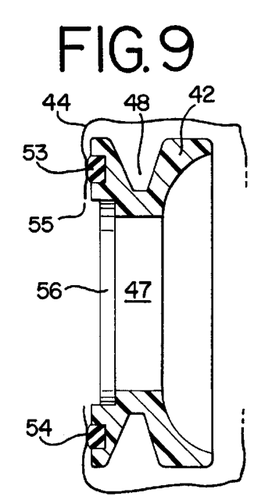
FIG. 9 shows the arrangement of FIG. 8 with a lens positioned in the first housing piece.
Figure 10:
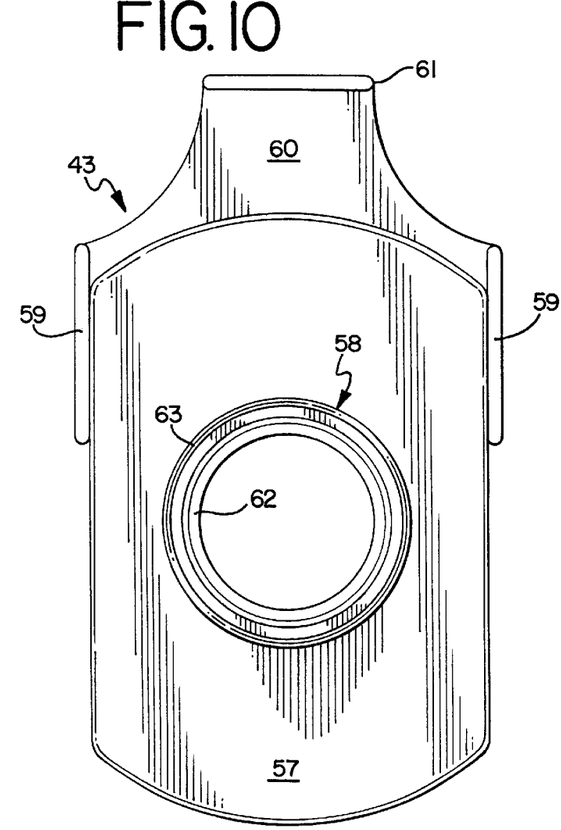
FIG. 10 shows a side view of the second housing piece of the drape of FIG. 4.

As can be seen from FIG. 7, a portion 44a of sheath 44 extends across the optical pathway provided by passage 47 in the first housing piece. In order to improve the optical clarity, it may be necessary to remove this portion of the sheath and this may be achieved by simply cutting that portion of the sheath away, as is shown in FIG. 9. Removing that portion of the sheath will result in a substantially circular hole being cut in the sheath, with the edges of the hole defined by the edge 55 of the sheath material, as shown in FIG. 9.

Once the part of the sheath 44 covering the central passage 47 has been removed, lens 56 is positioned in the first housing piece 42 such that the lens 56 rests on shoulders 52. The lens 56 may be affixed to the first housing piece 42 at this stage. Alternatively, the lens 56 may be affixed into the housing once the second housing piece 41 has been joined to the first housing piece 42.

Figure 11:
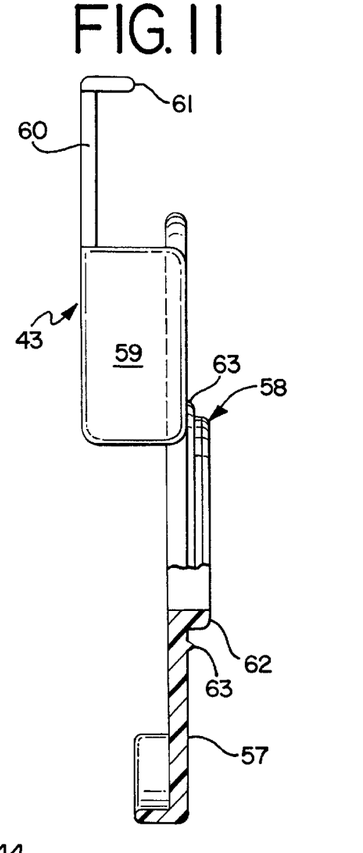
FIG. 11 is an end view of the second housing piece of FIG. 10.
Figure 12:
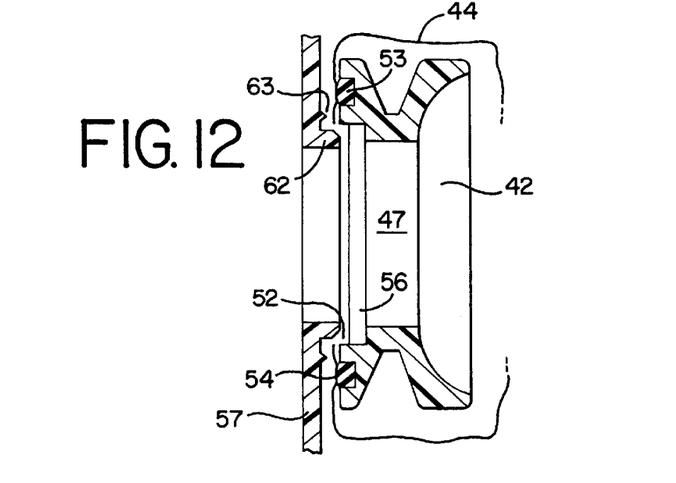
FIG. 12 is a side, cross-sectional view showing how the first and second housing pieces fit together.

FIGS. 11 and 12 show side and end views, respectively of second housing piece 43. Second housing piece 43 includes face 57 that includes a joining portion generally designated by reference numeral 58. Joining portion 58 will be described in greater detail hereunder. Second housing portion 41 also includes a rearwardly extending part 59 having a downwardly extending rear surface 60 and a stop member 61. Rearwardly extending portion 59, downwardly extending portion 60 and stop member 61 form a housing for a spring biased C coupling member (not shown) which is used to enable easy coupling of an endoscopic telescope to the second housing piece.

Turning now to consider the joining portion 58 in more detail, joining portion 58 includes a cylindrical projection 62 that is sized to fit relatively snugly inside the opening of the first housing piece 42 defined by the inner most annular portion 52. An energy director in the form of a circular ridge 63 is positioned a short distance away from the cylindrical projection 62. The energy director 63 substantially encircles cylindrical projection 62.

The fitment together of the first housing piece 41 and second housing piece 42 is best shown in FIG. 12, where it can be seen that cylindrical projection 62 on the face 57 of the second housing piece 41 fits into the recess formed by innermost annular portion 52. Energy director 63 comes into contact with the inner annular portion 51. Ultrasonic welding then takes place to join the first and second housing pieces together. As a result of the ultrasonic welding process, a joint similar to that shown in FIG. 3 is produced between the first and second housing pieces, which joint firmly joins the first and second housing pieces and also entraps the edges of the sheath.

Although not shown in any of the Figures, it is also possible that the housing could include a water tight gasket or seal that fits between the end of the endoscopic telescope and the housing. This water tight gasket or seal would act to prevent the ingress of water into the lens area of the housing, which would then minimise or avoid fogging on the lens of the housing.

Figure 13:
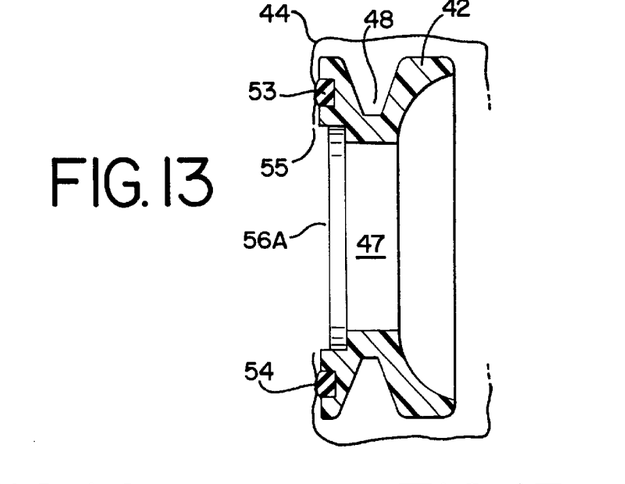
FIG. 13 is a view generally similar to that shown in FIG. 9 but with a corrective lens substituted for the flat lens of FIG. 9.

FIG. 13 shows a view generally similar to that of FIG. 9, with the difference being that the flat lens 56 of FIG. 9 has been replaced by the corrective lens 56A in FIG. 13. Accordingly, FIG. 13 is in accordance with the further aspect of the present invention. The corrective lens 56A preferably has a corrective power of 2 dioptive. The corrective lens 56A is incorporated into the housing when the first housing piece 42 is joined to the second housing piece 43. It is also possible to ultrasonically weld lens 56A to first housing piece 42 prior to joining the two housing pieces.

Figure 14:
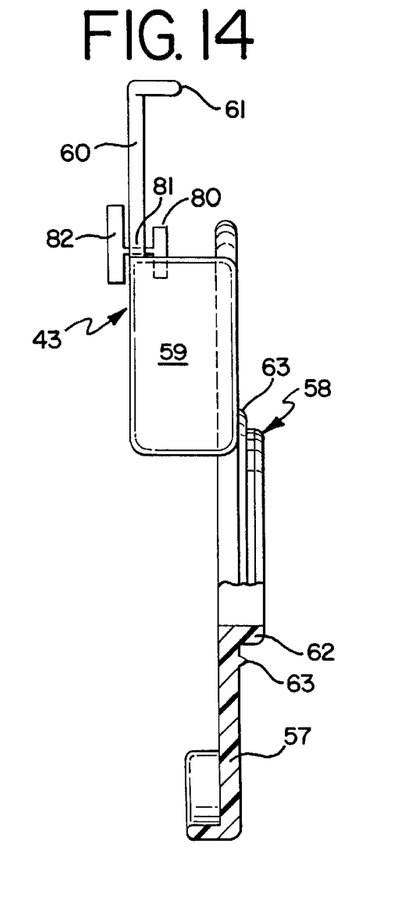
FIG. 14 is a side view of the second housing portion with a locking means incorporated therein in accordance with the present invention.
Figure 15:
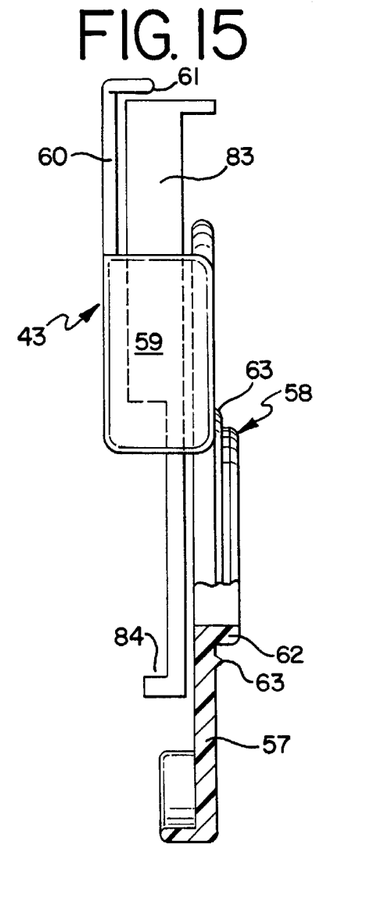
FIG. 15 shows the side view of FIG. 14 with the complete "C" coupling in place.
Figure 16:
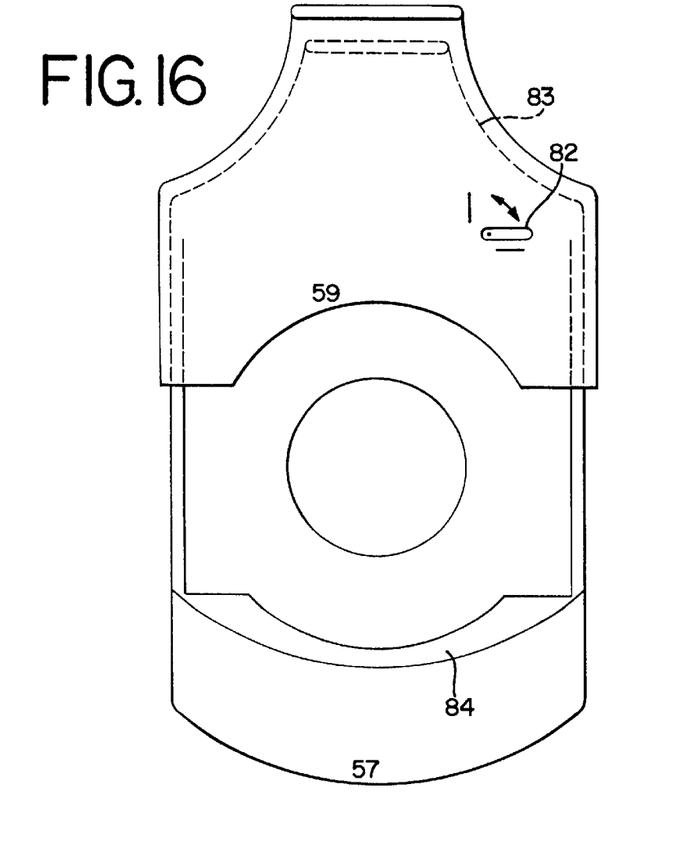
FIG. 16 is an end view of FIGS. 14 and 15.

Referring now to FIGS. 14, 15 and 16, FIGS. 14 and 15 show a side view of the second housing piece 43 with the full details of the "C" coupling added to FIG. 15. Dealing initially with FIG. 14, the locking mechanism of the second aspect of the invention comprises a rolling cam 80 mounted on pivot pin 81 and operable between an open position and a locked position by actuating switch 82. As best shown in FIGS. 15 and 16, in order to complete the "C" coupling, a movable body 83 having a lower engaging surface 84 is fitted and spring loaded into second housing piece 43. In particular, rearwardly extending portion 59, downwardly extending portion 60 and stop member 61 may be formed as a separate entity that snap fits onto second housing portion 43, for example, by having the leading edges of rearwardly extending portion 59 snap-fit onto face 57 of second housing piece 43. In order to complete the "C" coupling, the movable body 83 and associated spring (for spring loading—not shown) is positioned adjacent the face opposed to face 57 of second housing 30 piece 43 and the snap-fit entity comprising rearwardly extending portion 59, downwardly extending portion 69 and stop member 61 is fitted into place. In order to actuate the "C" coupling, movable body 83 is pushed downwardly to increase the distance between the lower part of rearwardly extending portion 59 and lower engaging surface 84i A telescope is mounted into this opening and lower engaging surface 84 allowed to move upwardly under the action of a spring (not shown) to capture and hold the end of the telescope between the rearwardly extending portion 59 and the lower engaging surface 84.

When the locking mechanism is in the open position, the rolling cam member 80 does not engage the movable body 80 and the telescope can be rotated. However, when moved to the locked position, rolling cam member 80 engaged movable body 83 and fixes it in position, thereby preventing rotational movement of the telescope (for the sake of clarity, the locking mechanism has been deleted from FIG. 15). In the unlocked position, when a telescope coupled to the second housing piece 43, the telescope, although connected to the second piece 43, can rotate within the telescope couplings. Generally, the telescope rotates around its own longitudinal axis. However, when the locking mechanism is moved to the locked position, the telescope coupled to the second housing piece 43 is locked such that it cannot rotate within the telescope coupling. This may be achieved in a number of ways in addition to that shown in FIGS. 14–16. For example, actuation of the actuating switch or a lever or tab may actuate a camming plate or wedging member that firmly locks the telescope in place against rotation. Alternatively, actuation of the tab or lever may move an interlocking protrusion into interlocking engagement with a complementary shaped depression or hole formed in the edge of the telescope. Obviously, a number of other suitable arrangements may also be used in the locking means.

Figure 17:
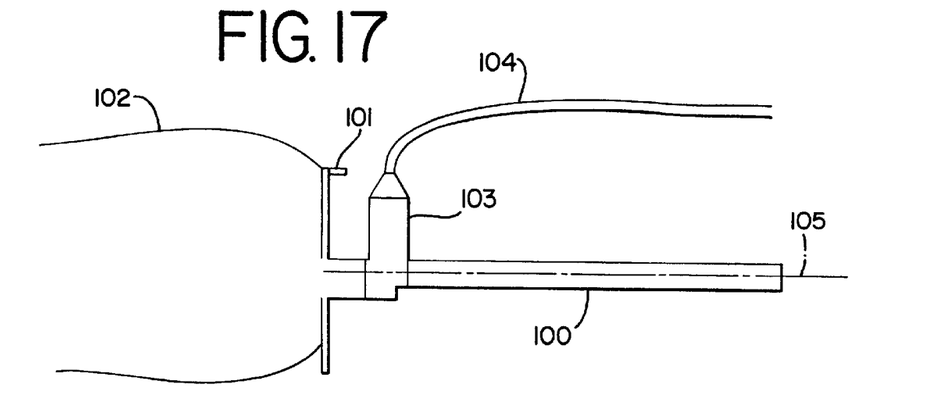
FIG. 17 is a side view of a telescope coupled to the housing with the sheath extended over the camera and accompanying cable.

Turning now to FIG. 17, this figure shows a telescope 100 connected to housing 101 with drape 102 extending over the camera and its associated cables. Telescope 100 includes a fibre optic port 103 having a fibre optic cable 104 connected thereto. Fibre optic cable 104 provides a source of light to the telescope 100. In the embodiment shown in FIG. 14, when the locking means is in the open position, the telescope 100 can rotate about its own longitudinal axis 105. However, it will be appreciated that if the telescope 100 rotates too far about its longitudinal axis, the fibre optic cable 104 will become wrapped around the telescope 100. Accordingly, it is preferred that, when in the open position, it is preferred that the telescope can only rotate through a restricted amount, with an amount of between 30 and 70 degrees either side of the original position being suitable. When the locking means is placed in the locked position, the telescope cannot rotate at all. In some operative procedures, it is of assistance to the surgeon if the telescope can be rotated. However, in other operative procedures, it is preferred that the telescope not be able to be rotated. Accordingly, provision of the locking means in FIG. 14, and in accordance with the second aspect of the present invention, allows the surgeon to select the preferred mode.

The apparatus of the present invention may provide an inexpensive means for optically coupling the camera and telescope together. The apparatus includes a superior connection between the sheath and the housing of the apparatus to ensure that a leak proof seal between the housing and the sheath is obtained.

It will be appreciated that the invention described herein is susceptible to variations and modifications other than those specifically described. It is to be understood that the invention encompasses all such variations and modifications that fall within its spirit and scope.

What is claimed is:

1. A method for manufacturing a drape for use in endoscopic surgical procedures, the method comprising the steps of positioning a portion of a sheath of flexible material adjacent to or in abutment with a thermoplastic material positioned on or near a joining portion of a first housing piece, positioning a joining portion of a second housing piece adjacent to or in abutment with the portion of the sheath and the joining portion of the first housing piece and joining the sheath to the thermoplastic and permanently joining the joining portion of the first housing piece and the second housing piece to thereby form a housing and entrap the portion of the sheath between the first housing piece and the second housing piece.

2. A method as claimed in claim 1 wherein the portion of the sheath is an end of the sheath.

3. A method as claimed in claim 1 wherein an edge of the portion of the sheath is entrapped between the first housing piece and the second housing piece.

4. A method as claimed in claim 1 further including the step of removing any material of the sheath extending across an optical pathway in the first housing piece prior to joining the first housing piece and the second housing piece.

5. A method as claimed in claim 1 further including the step of placing a lens in one of the first or second housing pieces prior to joining the first housing piece and the second housing piece.

6. A method as claimed in claim 5 wherein the lens is affixed to the one of the first or second housing pieces prior to joining the first housing piece and the second housing piece.

7. A method as claimed in claim 1 wherein the portion of the sheath does not fully cover or fully extend between the joining portions of the first and second housing piece whereby at least a part of one joining portion is in contact with at least a part of the other joining portion.

8. A method as claimed in claim 1 wherein the step of joining the joining portions comprises ultrasonic welding.

9. A method as claimed in claim 1 wherein the step of joining the sheath to the thermoplastic material comprises impulse welding.

10. A method as claimed in claim 1 wherein the portion of the sheath is welded to the thermoplastic material and the joining portions of the first and second housing pieces are also welded to each other to form the housing, the welding also joining the thermoplastic material to one or both of the first and second housing pieces.

11. A drape for use in an endoscopic procedure, the drape comprising a housing having a first housing piece permanently joined to a second housing piece, a thermoplastic material permanently joined to the housing between the first and second housing pieces and a sheath of flexible material, the sheath having a portion thereof joined to the thermoplastic material the sheath having a part thereof trapped between the joined first and second housing pieces, wherein a leak-proof seal is established between the sheath and the housing.

12. A drape as claimed in claim 11 wherein the portion of the sheath is an end of the sheath.

13. A drape as claimed in claim 11 wherein the housing includes an optical pathway therein.

14. A drape as claimed in claim 13 wherein a lens or window is positioned in the optical pathway.

15. A drape for use in an endoscopic surgical procedure, the drape comprising a housing including a first housing piece having a portion permanently joined to a joining portion of a second housing piece, a sheath of flexible material having a portion positioned between the first and second housing pieces, a thermoplastic material positioned between the portion of the sheath and one of the first and second housing pieces, the thermoplastic material affixing the portion of the sheath to one of the first and second housing pieces and wherein the joining portions of the first and second housing pieces surround and entrap an edge of the portion of the sheath in the completed housing.

16. A drape as claimed in claim 15 wherein a lens or window is positioned within the housing.

17. A drape as claimed in claim 11 or claim 15 further including a camera coupling for coupling a camera thereto.

18. A drape as claimed in claim 11 or claim 15 further including a telescope coupling for coupling an endoscopic telescope thereto.

19. A drape as claimed in claim 18 wherein the telescopic coupling comprises a "C"-coupling.

20. A drape as claimed in claim 18 wherein the telescope coupling includes locking means operative between a first position wherein a telescope is connected to the telescope coupling and can rotate within the telescope coupling and a second position wherein the telescope is connected to the telescope coupling and locked against rotation within the telescope coupling.

21. A drape as claimed in claim 20 wherein the telescope coupling comprises a movable body having an engaging surface, said movable body being fitted into the second housing piece of said housing, said movable body being movable from an open position in which the telescope can be inserted therein and removed therefrom and a closed position wherein said telescope is retained by said telescope coupling.

22. A drape as claimed in claim 21 wherein the locking means comprises a rolling cam mounted on a pivot pin, said rolling cam engaging said movable body in the locked position to thereby fix the telescope against rotational movement.

23. A drape as claimed in claim 21 wherein the locking means comprises a wedging member.

24. A drape as claimed in claim 21 wherein the locking means comprises a camming plate.

25. A drape as claimed in claim 11 or claim 15 wherein the thermoplastic material comprises a thermoplastic gasket or O-ring.

26. A drape as claimed in claim 25 wherein the thermoplastic gasket or O-ring is positioned in a groove on the one of the first or second housing pieces.

27. A drape as claimed in claim 11 or claim 15 wherein the sheath is substantially cylindrical.

28. A drape as claimed in claim 11 or claim 15 wherein the housing has an optical pathway therein to enable light and/or an image from an endoscopic telescope to be transmitted to a camera wherein a corrective lens is placed in the optical pathway.

29. A drape as claimed in claim 28 wherein the lens comprises an anti-fog lens or has an anti-fog coating applied thereto.

30. A drape as claimed in claim 28 wherein the lens has a corrective power sufficient to produce an in-focus picture on a visual display unit during an operative procedure.

31. A drape as claimed in claim 30 wherein the lens has a power of from 1–10 dioptive.

32. A drape as claimed in claim 30 wherein the lens has a power of about 2.0 dioptive.

* * * * *